United States Patent
Kamakura

(10) Patent No.: US 10,285,266 B2
(45) Date of Patent: May 7, 2019

(54) DETECTION DEVICE

(71) Applicant: Seiko Epson Corporation, Tokyo (JP)

(72) Inventor: Tomoyuki Kamakura, Matsumoto (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/911,793

(22) Filed: Mar. 5, 2018

(65) Prior Publication Data

US 2018/0279467 A1   Sep. 27, 2018

(30) Foreign Application Priority Data

Mar. 23, 2017   (JP) ................................. 2017-057440

(51) Int. Cl.
   *H05K 1/02*    (2006.01)
   *H05K 1/14*    (2006.01)
   *A61B 5/00*    (2006.01)
   *A61B 5/024*   (2006.01)

(52) U.S. Cl.
   CPC ....... *H05K 1/0281* (2013.01); *A61B 5/02438* (2013.01); *A61B 5/681* (2013.01); *H05K 1/144* (2013.01); *A61B 2562/0219* (2013.01)

(58) Field of Classification Search
   CPC .. H05K 1/0283; H05K 1/0277; H05K 1/0281; H05K 1/144; A61B 5/02438; A61B 5/681; A61B 2562/0219
   See application file for complete search history.

(56) References Cited

U.S. PATENT DOCUMENTS

| | | | | |
|---|---|---|---|---|
| 2008/0257589 A1* | 10/2008 | Ostmann | ............... | H05K 1/0271 174/254 |
| 2010/0294552 A1* | 11/2010 | Kobayashi | ........ | H01L 23/49827 174/260 |
| 2011/0080713 A1* | 4/2011 | Sunohara | .............. | H01L 23/147 361/760 |
| 2014/0340857 A1* | 11/2014 | Hsu | ....................... | H05K 1/0283 361/749 |
| 2017/0034907 A1* | 2/2017 | Iwase | ................... | H05K 1/0283 |

(Continued)

FOREIGN PATENT DOCUMENTS

JP     2008-147246 A   6/2008
JP     2013-145842 A   7/2013

(Continued)

*Primary Examiner* — Steven T Sawyer
(74) *Attorney, Agent, or Firm* — Harness, Dickey & Pierce, P.L.C.

(57) ABSTRACT

A detection device includes: an expanding and contracting base having elasticity; a first base which is provided to overlap the expanding and contracting base, has a Young's modulus higher than that of the expanding and contracting base, and includes a connection portion to which a sensing section is connectable; a second base which is provided on a side of the expanding and contracting base opposite to the first base, and has a Young's modulus higher than that of the expanding and contracting base; a connection member which electrically connects the expanding and contracting base and the first base to each other; and a mold portion which is provided to come into contact with the connection member, has a Young's modulus higher than that of the expanding and contracting base, and has a Young's modulus lower than that of the first base.

8 Claims, 6 Drawing Sheets

(56) References Cited

U.S. PATENT DOCUMENTS

2017/0099730 A1    4/2017  Iwase
2018/0084643 A1*   3/2018  Baxi .................... H05K 1/0283

FOREIGN PATENT DOCUMENTS

| JP | 5823879 B2    | 11/2015 |
| JP | 2017-034038 A | 2/2017  |
| JP | 2017-069530 A | 4/2017  |
| JP | 2017-143257 A | 8/2017  |

* cited by examiner

DETECTION DEVICE

BACKGROUND

1. Technical Field

The present invention relates to a detection device.

2. Related Art

For example, JP-A-2013-145842 discloses a flexible circuit substrate including: an expandable and contractible circuit body which is provided with an expandable and contractible wiring portion on an expandable and contractible insulating base material; and a non-expandable and non-contractible component mounting substrate laminated on a predetermined region of the expandable and contractible circuit substrate. With such a configuration, the wiring can be expanded and contracted, and can be appropriately used for a movable portion of a robot or the like.

However, when the expansion and contraction of the expandable and contractible circuit body is frequently repeated, breakage or the like occurs between the expandable and contractible circuit body and the component mounting substrate, and the electric connection between the wiring portion and the component mounting substrate is lost in some cases.

Meanwhile, from the viewpoint of preventing the breakage of the flexible printed substrate, as disclosed in JP-A-2008-147246, a structure in which a rigid substrate is mounted on the flexible printed substrate and a reinforcing plate is provided on a surface opposite to the rigid substrate of the flexible printed substrate, is known. With the structure, the robustness of the flexible printed substrate is enhanced and breakage is prevented.

However, the structure disclosed in JP-A-2008-147246 is insufficient from the viewpoint of robustness in a case where the flexible printed substrate is frequently expanded and contracted, resulting in defects, such as a loss of electric connection.

SUMMARY

An advantage of some aspects of the invention is to provide a detection device in which a loss of electric connection due to expansion and contraction of an expanding and contracting base is unlikely to occur.

The advantage can be achieved by the following configurations.

A detection device according to an aspect of the invention includes: an expanding and contracting base having elasticity; a first base which is provided to overlap the expanding and contracting base, has a Young's modulus higher than that of the expanding and contracting base, and includes a connection portion to which a sensing section is connectable; a second base which is provided on a side of the expanding and contracting base opposite to the first base, and has a Young's modulus higher than that of the expanding and contracting base; a connection member which electrically connects the expanding and contracting base and the first base to each other; and a mold portion which is provided to come into contact with the connection member, has a Young's modulus higher than that of the expanding and contracting base, and has a Young's modulus lower than that of the first base.

With this configuration, a detection device in which a loss of electric connection due to expansion and contraction of the expanding and contracting base is unlikely to occur, is obtained.

In the detection device according to the aspect of the invention, it is preferable that the expanding and contracting base includes a wiring having elasticity.

With this configuration, the expansion and contraction of the expanding and contracting base becomes easy, and the wiring becomes unlikely to be disconnected according to the expansion and contraction.

In the detection device according to the aspect of the invention, it is preferable that the wiring includes a recessed portion, and the connection member is fitted into the recessed portion.

With this configuration, while the connection member and the wiring are electrically connected to each other, a positional shift to a certain extent is allowed therebetween. Therefore, even when the expanding and contracting base expands and contracts and mutual positional shift occurs between the recessed portion and the connection member, the shift is absorbed and the electric connection is unlikely to be lost.

In the detection device according to the aspect of the invention, it is preferable that a sensing section which is connected to the connection portion and detects a change in electric resistance of the wiring, is further provided.

With this configuration, it is possible to acquire a change amount of electric resistance, and to acquire the change amount by converting the amount into an expansion and contraction amount of the expanding and contracting base.

In the detection device according to the aspect of the invention, it is preferable that the second base is a coating film.

With this configuration, it is possible to further enhance the adhesion between the second base and the expanding and contracting base. In other words, since a gap therebetween is unlikely to be generated, the reinforcing effect of the expanding and contracting base by the second base is further strengthened.

In the detection device according to the aspect of the invention, it is preferable that the mold portion is provided to come into contact with the connection member, the expanding and contracting base, and the first base.

With this configuration, the expanding and contracting base and the first base are bonded to each other via the mold portion, and it is possible to reinforce the expanding and contracting base with a wider area, and to more reliably suppress the expansion and contraction amount.

In the detection device according to the aspect of the invention, it is preferable that the connection member is provided between the expanding and contracting base and the first base.

With this configuration, it is possible to minimize the area occupied by the connection member. In other words, since the connection member is hidden behind the first base, the connection member does not protrude, and accordingly, the size of the detection device can be minimized.

In the detection device according to the aspect of the invention, it is preferable that, when the first base, the second base, the connection member, and the mold portion are made in a unit, the plurality of units are provided for the expanding and contracting base.

With this configuration, it is possible to obtain a detection device in which units with different functions are provided, and which has a higher added value with more functions.

In the detection device according to the aspect of the invention, it is preferable that the detection device is a vital sensor.

With this configuration, a vital sensor having high reliability can be obtained.

In the detection device according to the aspect of the invention, it is preferable that the detection device is a motion sensor.

With this configuration, a motion sensor having high reliability can be obtained.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, appropriate embodiments of a detection device according to the invention will be described with reference to the attached drawings.

First Embodiment

First, a detection device according to a first embodiment of the invention will be described.

Figure 1:
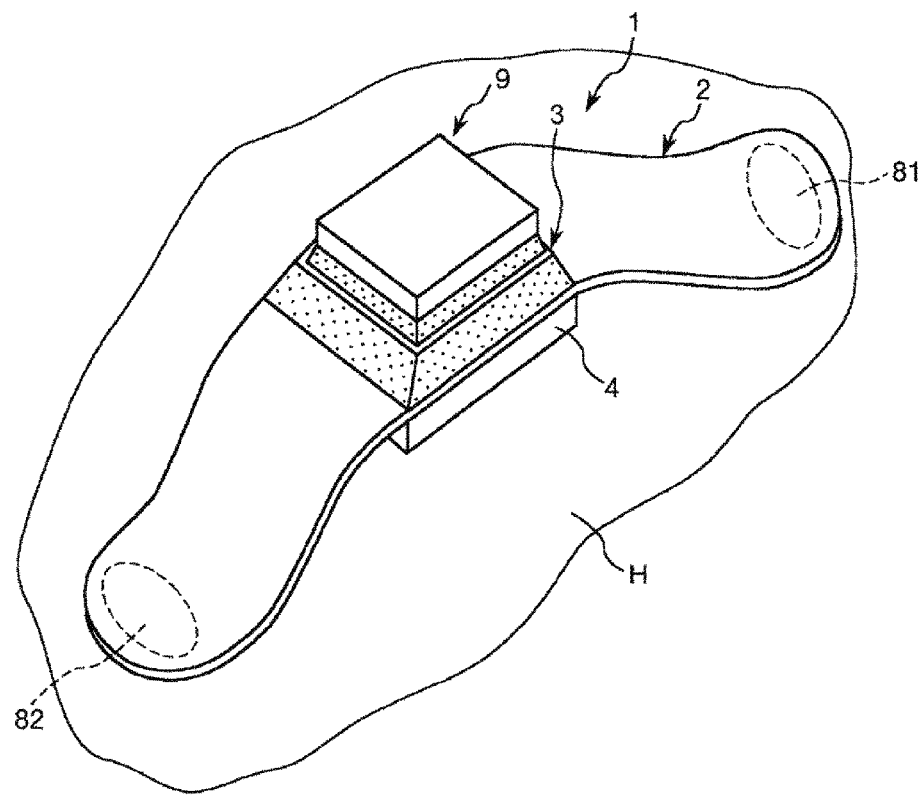
FIG. 1 is a perspective view of a detection device according to a first embodiment of the invention.
Figure 2:
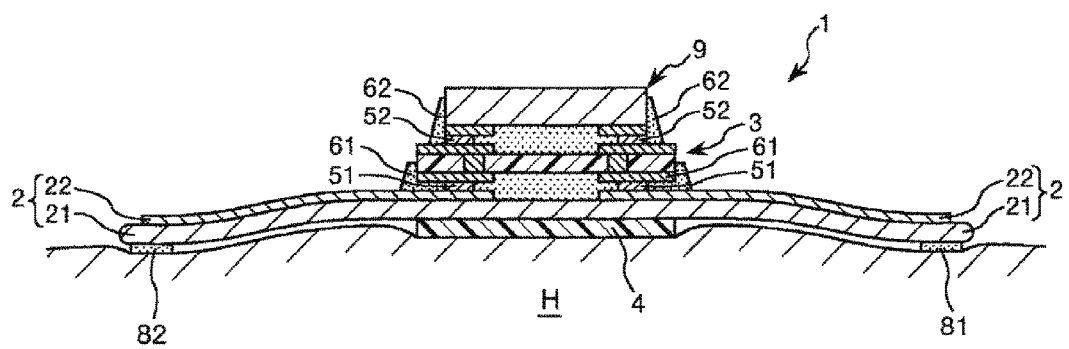
FIG. 2 is a sectional view of the detection device illustrated in FIG. 1.
Figure 3:
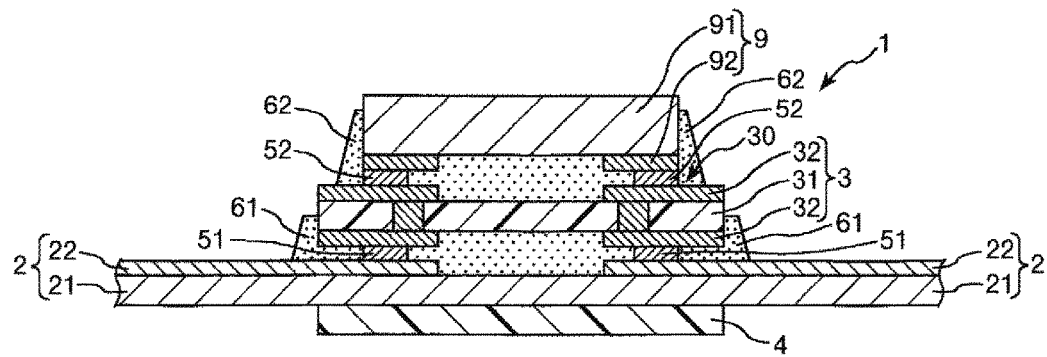
FIG. 3 is a partially enlarged view of FIG. 2.

FIG. 1 is a perspective view of the detection device according to the first embodiment of the invention. FIG. 2 is a sectional view of the detection device illustrated in FIG. 1. FIG. 3 is a partially enlarged view of FIG. 2.

A detection device 1 illustrated in FIG. 1 is a wearable terminal which is used while being mounted on a movable body and is usable as a motion sensor which detects the movement of the movable body. In addition, the movable body is not particularly limited, and various moving objects, such as various animals including a human, various robots having joints, automobiles, airplanes, and the like can be employed. In addition, in the embodiment, for convenience of explanation, a case where the movable body is a human H will be described as an example.

As illustrated in FIGS. 2 and 3, the detection device 1 includes: an expanding and contracting base 2 having elasticity; first base 3 which is provided to overlap the expanding and contracting base 2; a second base 4 which is provided on a side of the expanding and contracting base 2 opposite to the first base 3; a connection member 51 which electrically connects the expanding and contracting base 2 and the first base 3 to each other; and a mold portion 61 which is provided to come into contact with the connection member 51. In addition, the first base 3 includes a connection portion 30 which has a Young' s modulus higher than that of the expanding and contracting base 2, and to which a sensing section 9 is connectable. In addition, in the second base 4, a Young's modulus is higher than that of the expanding and contracting base 2. In addition, the mold portion 61 has a Young's modulus higher than that of the expanding and contracting base 2, and has a Young's modulus lower than that of the first base 3.

As illustrated in FIGS. 1 and 2, the detection device 1 is mounted on a surface (for example, the skin) of the human H. When the expanding and contracting base 2 expands and contracts with the bending and stretching of the joint, a resistance value of the wiring included in the expanding and contracting base 2 changes in accordance with the degree of expansion and contraction. By detecting the change in resistance value with the sensing section 9, it is possible to detect the movement (joint motion) of the human H. In other words, the detection device 1 functions as a motion sensor.

In the above-described use method, the expanding and contracting base 2 frequently expands and contracts. At this time, according to the above-described configuration, a structure in which the expanding and contracting base 2 is sandwiched between the first base 3 and the second base 4, each of which has a Young's modulus higher than that of the expanding and contracting base 2. With the structure, since the expansion and contraction of the expanding and contracting base 2 is partially suppressed, the electric connection between the expanding and contracting base 2 and the first base 3 via the connection member 51 is unlikely to be damaged. Therefore, a motion sensor having high reliability can be obtained.

In addition, in a case where the expansion and contraction amount of the expanding and contracting base 2 reflects the momentum of the human H, the detection device 1 can be used as a vital sensor. Accordingly, it is possible to monitor the momentum of the human H who has the detection device 1 mounted thereon, and to detect vital abnormality. In addition, similar to the description above, a vital sensor having high reliability can be obtained.

Meanwhile, the mold portion 61 having a Young's modulus higher than that of the expanding and contracting base 2 is provided to come into contact with the connection member 51, and accordingly, concentration of stress at an outer edge of the connection member 51 is mitigated by the mold portion 61. Accordingly, breakage starting from the outer edge of the connection member 51 is unlikely to occur, and from this point of view, the loss of the electric connection between the expanding and contracting base 2 and the first base 3 via the connection member 51 is also suppressed.

Hereinafter, the detection device 1 will be described in more detail.

As described above, the expanding and contracting base 2 is a part to be stuck over the position with respect to a position where the movement is desired to be detected, such as a joint. The expanding and contracting base 2 has elasticity and can be deformed following the surface of the human H at the time of mounting, and can expand and contract in accordance with the movement of the human H. In addition, the expanding and contracting base 2 has a long strip shape, one end portion thereof is bonded to the surface of the human H via a bonding pad 81, and the other end portion is bonded to the surface of the human H via a bonding pad 82. In addition, the mounting method is not particularly limited.

The expanding and contracting base 2 illustrated in FIG. 2 is provided with an expanding and contracting insulating substrate 21 and a wiring 22. The wiring 22 is provided on the surface of the expanding and contracting insulating substrate 21. In addition, both of the expanding and contracting insulating substrate 21 and the wiring 22 may be configured to integrally expand and contract, or may be configured to individually expand and contract.

A configuration material of the expanding and contracting insulating substrate 21 is not particularly limited as long as the expanding and contracting insulating substrate 21 can exhibit elasticity, and for example, various types of thermoplastic elastomers, such as polyurethane type elastomer, styrene type thermoplastic elastomer, olefin type thermoplastic elastomer, vinyl chloride type thermoplastic elastomer, ester type thermoplastic elastomer, amide type thermoplastic elastomer, and fluorine type thermoplastic elastomer; and various types of rubber materials, such as acrylic rubber, silicone type rubber, butadiene type rubber, and styrene type rubber, can be used.

The wiring 22 has elasticity in the longitudinal direction, and expands and contracts according to the expansion and contraction of the expanding and contracting insulating substrate 21. In other words, the expanding and contracting base 2 is provided with the wiring 22 having elasticity. Accordingly, the expansion and contraction of the expanding and contracting base 2 becomes easy, and the wiring 22 becomes unlikely to be disconnected according to the expansion and contraction.

A configuration material of the wiring 22 is not particularly limited, but for example, a conductive resin material in which various types of thermoplastic elastomers, such as polyurethane type elastomer, styrene type thermoplastic elastomer, olefin type thermoplastic elastomer, vinyl chloride type thermoplastic elastomer, ester type thermoplastic elastomer, amide type thermoplastic elastomer, and fluorine type thermoplastic elastomer; and various types of rubber materials, such as acrylic rubber, silicone type rubber, butadiene type rubber, and styrene type rubber, are mixed with various types of conductive fillers, such as a metal base (for example, Au, Ag, Cu, Ni, Zn, and Al), a metal oxide base (for example, $SnO_2$/Sb-doped, $In_2O_3$/Sn-doped, and ZnO/Al-doped), carbon based (for example, conductive carbon black and graphite), can be used. In addition, by adding cellulose nanofibers, carbon nanofibers or the like to the above-described material, the resin is reinforced, and the wiring 22 which is unlikely to be disconnected can be obtained.

In addition, the wiring 22 illustrated in FIGS. 1 and 2 is divided into two systems toward both sides in the longitudinal direction of the expanding and contracting base 2 via the first base 3. A pattern of the wiring 22 is not particularly limited, and any pattern may be used.

For example, although not illustrated, the two systems of wiring 22 may be a pattern folded back at the end portion of the expanding and contracting base 2, respectively. In other words, the two wirings 22 on each of the left and right sides illustrated in FIG. 5 may be connected to each other at each of the ends.

The first base 3 is provided so as to overlap the expanding and contracting base 2 as described above.

In addition, the expanding and contracting base 2 and the first base 3 may be fixed to each other, or may be bonded to each other via an inclusion, such as an adhesive, but in FIG. 2, the expanding and contracting base 2 and the first base 3 are electrically and mechanically connected to each other via the connection member 51. Furthermore, although the mold portion 61 fills a space between the expanding and contracting base 2 and the first base 3 illustrated in FIG. 2, but mutual adhesion is also achieved by the mold portion 61.

The first base 3 has a Young's modulus higher than that of the expanding and contracting base 2. By providing the first base 3 so as to overlap the expanding and contracting base 2, it is possible to partially suppress the expansion and contraction of the expanding and contracting base 2 in cooperation with the second base 4. Therefore, the connection member 51 which electrically connects the first base 3 and the expanding and contracting base 2 to each other loses the electric connection according to the expansion and contraction of the expanding and contracting base 2, or the electric resistance is prevented from being raised.

In addition, a Young's modulus of the first base 3 may be higher than a Young's modulus of the expanding and contracting base 2, but the difference between both of the Young's moduli is preferably set to 100 MPa or more, and is more preferably set to 300 MPa or more and 3 GPa or less. By keeping the difference of a Young's modulus within the range, it is possible to sufficiently suppress the expansion and contraction of the expanding and contracting base 2 by the first base 3, a certain degree of deformability is also given to the first base 3, and accordingly, the first base 3 is unlikely to be peeled off from the expanding and contracting base 2.

In addition, a Young's modulus of the first base 3 and a Young's modulus of the expanding and contracting base 2 are measured in accordance with, for example, the measuring method of tensile elastic modulus specified in JIS K 7161-2014.

As illustrated in FIG. 3, the first base 3 includes an insulating section 31 and a conductive portion 32. The conductive portion 32 is provided in a through-hole which penetrates the surface of the insulating section 31 and the insulating section 31. By the conductive portion 32, a wiring pattern is formed on the first base 3.

As the insulating section 31, although not particularly limited, for example, a glass epoxy substrate, a glass composite substrate, a ceramic substrate or the like is used. In addition, a substrate containing a relatively hard resin, such as a polyimide resin, an epoxy resin, a phenol resin, a polyamide resin, a polycarbonate resin, or polyethylene terephthalate; or a glass substrate, may be employed.

As a configuration material of the conductive portion 32, although not particularly limited, for example, a simple substance of a metal material, such as Au, Ag, Cu, Ni, Zn, and Al or an alloy including these (including a mixed metal and an intermetallic compound) ; a metal oxide material, such as $SnO_2$/Sb-doped, $In_2O_3$/Sn-doped, and ZnO/Al-doped; and a carbon material, such as conductive carbon black and graphite, are employed, and one or more of the composites are used. In addition, as an aspect, a form of a foil or a form of a coated film may be employed.

In addition, the first base 3 includes the connection portion 30 which is capable of connecting the sensing section 9 which will be described later. The connection portion 30 includes a terminal or the like for electrically connecting the sensing section 9. The terminal is connected to the conductive portion 32. Accordingly, the wiring 22 is electrically connected to the sensing section 9 via the conductive portion 32 or the terminal.

In addition, the first base 3 is not limited to the illustrated configuration, and for example, may a multilayer substrate, or may include a wiring pattern therein.

In addition, the first base 3 is not only a member to which a substrate or a film is pasted but also a member formed by applying a liquid material and curing or solidifying the material.

As described above, the second base 4 is provided on a side of the expanding and contracting base 2 opposite to the first base 3. The expanding and contracting base 2 and the second base 4 may be fixed to each other, or may adhere to each other via an inclusion, such as an adhesive.

The second base 4 has a Young's modulus higher than that of the expanding and contracting base 2. By providing the second base 4 on the side of the expanding and contracting base 2 opposite to the first base 3, it is possible to construct a structure in which the expanding and contracting base 2 is sandwiched together with the first base 3. With the structure, it is possible to partially suppress the expansion and contraction of the expanding and contracting base 2. Therefore, the connection member 51 which electrically connects the first base 3 and the expanding and contracting base 2 to each other can prevent the electric connection from being lost according to the expansion and contraction of the expanding and contracting base 2, or the electric resistance from being raised.

In addition, a Young's modulus of the second base 4 may be higher than a Young's modulus of the expanding and contracting base 2, but the difference between both of the Young's moduli is preferably set to 100 MPa or more, and is more preferably set to 300 MPa or more and 3 GPa or less. By keeping the difference of a Young's modulus within the range, it is possible to sufficiently suppress the expansion and contraction of the expanding and contracting base 2 by the second base 4, a certain degree of deformability is also given to the second base 4, and accordingly, the second base 4 is unlikely to be peeled off from the expanding and contracting base 2.

Meanwhile, a Young's modulus of the second base 4 maybe higher or lower than a Young's modulus of the first base 3, and may be set to the same extent.

In addition, a Young's modulus of the second base 4 is measured in accordance with, for example, the measuring method of tensile elastic modulus specified in JIS K 7161-2014.

As the second base 4, although not particularly limited, for example, a glass epoxy substrate, a glass composite substrate, a ceramic substrate or the like is used. In addition, a substrate containing a relatively hard resin, such as a polyimide resin, an epoxy resin, a phenol resin, a polyamide resin, a polycarbonate resin, or polyethylene terephthalate; or a glass substrate, may be employed.

In addition, the second base 4 may include a wiring pattern.

In addition, the second base 4 is not only a member to which a substrate or a film is pasted but also a member formed by applying a liquid material and curing or solidifying the material.

As described above, the connection member 51 electrically connects the expanding and contracting base 2 and the first base 3 to each other. Accordingly, the expanding and contracting base 2 and the sensing section 9 are electrically connected to each other via the first base 3, and detection of change in resistance value by sensing section 9 becomes possible.

The connection member 51 may be any member as long as the expanding and contracting base 2 and the first base 3 can be electrically connected to each other, but preferably, as illustrated in FIG. 3, a bump which protrudes from the first base 3 to the expanding and contracting base 2 side is employed. Since the bump preferentially comes into contact with the expanding and contracting base 2, the bump is useful from the viewpoint of more reliable connection.

Figure 4:
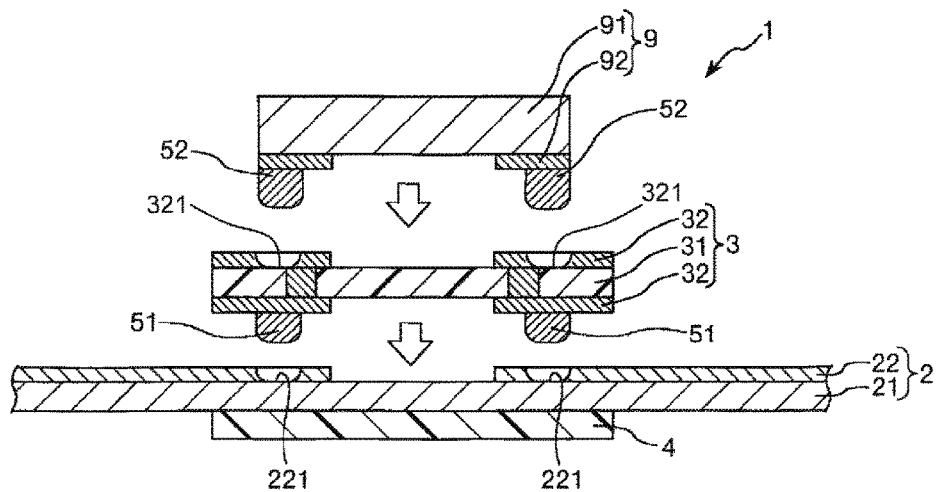
FIG. 4 is a modification example of an exploded sectional view of the detection device illustrated in FIG. 3.
Figure 5:
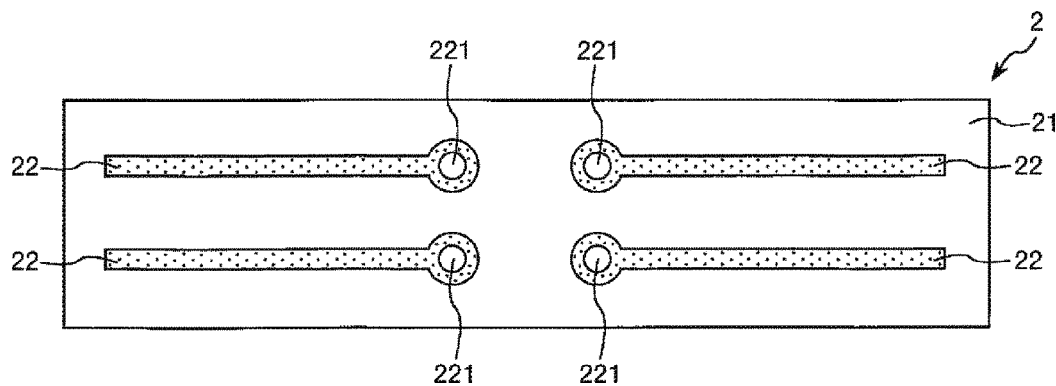
FIG. 5 is a top view of an expanding and contracting base included in the detection device illustrated in FIG. 4.

Here, FIG. 4 is a modification example of an exploded sectional view of the detection device 1 illustrated in FIG. 3. In addition, FIG. 5 is a top view of the expanding and contracting base 2 included in the detection device 1 illustrated in FIG. 4. In addition, in FIG. 4, the mold portion 61 is omitted.

The wiring 22 included in the expanding and contracting base 2 may include any connection structure as long as the wiring 22 comes into contact with the connection member 51 as illustrated in FIG. 3. For example, as illustrated in FIGS. 4 and 5, a recessed portion 221 formed by recessing the upper surface may be included. The recessed portion 221 may be formed by recessing the upper surface of the wiring 22, but may be formed so as to penetrate the wiring 22.

In addition, it is preferable that the above-described bump (connection member 51) is fitted into the recessed portion 221 when being assembled as illustrated by an arrow in FIG. 4. Accordingly, while the connection member 51 and the wiring 22 are electrically connected to each other, a positional shift to a certain extent is allowed therebetween. In other words, when the connection member 51 is fitted into the recessed portion 221, the contact state therebetween is maintained, and thus, the electric connection is achieved, but even when the connection member 51 is shifted with respect to the recessed portion 221, unless the connection member 51 comes off from the recessed portion 221, the electric connection is maintained. Therefore, a structure in which, even when the expanding and contracting base 2 expands and contracts and mutual positional shift occurs between the recessed portion 221 and the connection member 51, the shift is absorbed and the electric connection is unlikely to be lost, is achieved.

In addition, from this point of view, in order to make the surface of the connection member 51 and the inner surface of the recessed portion 221 easily come into contact with each other, the sizes of both of the surfaces may be appropriately set.

In addition, the shape of the wiring 22 in a plan view is not limited to a linear shape as illustrated in FIG. 5, and may be, for example, a shape including a curve, a waveform shape (meandering shape), or a spiral shape.

A case where the expanding and contracting base 2 and the first base 3 are electrically connected to each other, includes not only an aspect in which both of the bases are directly linked to each other by the connection member 51 but also an aspect in which both of the bases are conducted to each other by interposing other members therebetween.

As a configuration material of the connection member 51, for example, a simple substance of a metal material, such as Au, Ag, Cu, Ni, Zn, and Al or an alloy including these (including a compound and an intermetallic compound); a metal oxide material, such as $SnO_2$/Sb-doped, $In_2O_3$/Sn-doped, and ZnO/Al-doped; and a carbon material, such as conductive carbon black and graphite, are employed, and one or more of the composites are used.

In addition, the connection member 51 is not limited to the above-described configuration. For example, the connection member 51 may be a bonding metal, such as a solder or a brazing filler metal, or an anisotropic conductive sheet or an anisotropic conductive paste.

In addition, the disposition of the connection member 51 is not particularly limited, but in FIG. 2, the connection member 51 is between the expanding and contracting base 2 and the first base 3. The connection member 51 is provided at the position, and accordingly, it is possible to minimize the area occupied by the connection member 51. In other words, since the connection member 51 is hidden behind the first base 3, the connection member 51 does not protrude, and accordingly, the size of the detection device 1 can be minimized.

As described above, the mold portion 61 is provided to come into contact with the connection member 51. By the mold portion 61, the concentration of stress at the outer edge of the connection member 51 is mitigated, and breakage starting from the outer edge of the connection member 51 is suppressed.

The mold portion 61 has a Young's modulus higher than that of the expanding and contracting base 2, and has a Young's modulus lower than that of the first base 3. By providing the mold portion 61, it is possible to sufficiently ensure a reinforcement function of the expanding and contracting base 2 by the first base 3, while suppressing the expansion and contraction operation of the expanding and contracting base 2 from being obstructed by the mold portion 61. As a result, it is possible to establish both of high elasticity of the expanding and contracting base 2 and suppression of the partial expansion and contraction amount by the first base 3, and to improve the reliability of the detection device 1 while improving the detection accuracy of the detection device 1.

In addition, the mold portion 61 reinforces the connection member 51, and it is possible to suppress the occurrence of breakage in which an interface between the connection member 51 and the expanding and contracting base 2 peels off starting from the outer edge of the connection member 51.

In addition, a Young's modulus of the mold portion 61 may be higher than a Young's modulus of the expanding and contracting base 2, but the difference between both of the Young's moduli is preferably set to 50 MPa or more, and is more preferably set to 100 MPa or more and 2 GPa or less. By keeping the difference of a Young's modulus within the above-described range, it is possible to sufficiently suppress the expansion and contraction of the expanding and contracting base 2 by the mold portion 61, and to sufficiently reinforce the connection member 51.

In addition, a Young's modulus of the mold portion 61 may be lower than a Young's modulus of the first base 3, but the difference between both of the Young's moduli is preferably set to 50 MPa or more, and is more preferably set to 100 MPa or more and 2 GPa or less. By keeping the difference of a Young's modulus within the above-described range, it is possible to sufficiently suppress the expansion and contraction of the expanding and contracting base 2 by the first base 3 via the mold portion 61.

In addition, a Young's modulus of the mold portion 61 is measured in accordance with, for example, the measuring method of tensile elastic modulus specified in JIS K 7161-2014.

In addition, the mold portion 61 may be provided to come into contact at least with the connection member 51, but further, as illustrated in FIG. 3, the mold portion 61 may be provided between the expanding and contracting base 2 and the first base 3. In other words, the mold portion 61 may be provided to come into contact with the connection member 51, the expanding and contracting base 2, and the first base 3. Accordingly, the expanding and contracting base 2 and the first base 3 are bonded to each other via the mold portion 61, and it is possible to reinforce the expanding and contracting base 2 with a wider area, and to more reliably suppress the expansion and contraction amount.

The sensing section 9 is an integrated circuit (IC) which is capable of detecting a change in resistance value of the wiring 22 included in the expanding and contracting base 2, for example. The sensing section 9 illustrated in FIG. 3 includes a sensor chip 91 and a terminal 92 provided on a lower surface of the sensor chip 91.

The sensing section 9 is installed on the connection portion 30 of the first base 3. In other words, the detection device 1 illustrated in FIG. 3 includes the sensing section 9 which is connected to the connection portion 30 and detects a change in electric resistance of the wiring 22. By providing the sensing section 9, it is possible to detect the change in electric resistance, and to acquire the change amount. In addition, it is also possible to obtain the change amount by converting the amount into the expansion and contraction amount of expanding and contracting base 2.

As a calculating method of the expansion and contraction amount by the sensing section 9, for example, a calculating method of the expansion and contraction amount based on a difference between a reference value and the resistance value detected in real time by comparing the reference value and the resistance value to each other after storing the resistance value of the wiring 22 when the expanding and contracting base 2 is in a reference state as the reference value. At this time, the conversion from the change amount of the resistance value into the expansion and contraction amount is performed based on a previously found relational expression, and the expansion and contraction amount may be corrected based on various pieces of information when necessary.

In other words, the terminal 92 and the connection portion 30 (conductive portion 32) are connected to each other via a connection member 52.

The configuration material of the connection member 52 is not particularly limited, but is appropriately selected from the materials listed as configuration materials of the connection member 51.

In addition, as illustrated in FIG. 3, the connection member 52 may include any connection structure as long as the connection member 52 comes into contact with the conductive portion 32, but as illustrated in FIG. 4, the connection member 52 may have a connection structure in which the connection member 52 is fitted into the conductive portion 32 in which a recessed portion 321 is formed. Accordingly, while the connection member 52 and the conductive portion 32 are electrically connected to each other, a positional shift to a certain extent is allowed therebetween. As a result, the connection structure is unlikely to lose the electric connection.

In addition, by employing the connection structure by fitting as described above, it is possible to easily release the connection state and connect the members again. Therefore, for example, when exchanging the expanding and contracting base 2 or the first base 3 for a new base, it is possible to easily perform the exchange work.

In addition, the connection structure is not limited to the above-described configuration, and any connection structure maybe used as long as the connection structures can be fitted into each other.

In addition, the periphery of the sensing section 9 and a space between the sensing section 9 and the first base 3 illustrated in FIG. 3 are covered with the mold portion 62, respectively. By providing the mold portion 62, it is possible to reinforce the connection member 52, and to suppress damage to this part.

Furthermore, since the sensing section 9 and the first base 3 are bonded to each other via the mold portion 62, it is possible to further enhance the reliability of the detection device 1.

In addition to the sensing section 9, the first base 3 may be provided with a battery that serves as a power source of the detection device 1, a storage section which stores the detected information therein, a communication section which outputs the detected information to the outside, and the like. Among these, as the storage section, for example, a flash memory or the like can be employed. In addition, a communication unit of the communication section may be wireless or wired, but wireless communication, such as Bluetooth (registered trademark), may be employed.

In addition, the detection device 1 may have a function for obtaining other information instead of the expansion and contraction amount. Examples of other information include biological information, such as electrocardiogram, myoelectric potential, body temperature, blood pressure, heartbeat, pulse wave, blood flow, and the like.

In addition, the detection device 1 may be provided with various sensors, such as a thermistor, an acceleration sensor, a gyro sensor, or the like, according to the information to be obtained. The sensors are electrically connected to, for example, the wiring 22, and the information to be obtained by the various sensors is used in processing, such as an arithmetic operation, in the sensing section 9.

Second Embodiment

Next, a detection device according to a second embodiment of the invention will be described.

Figure 6:
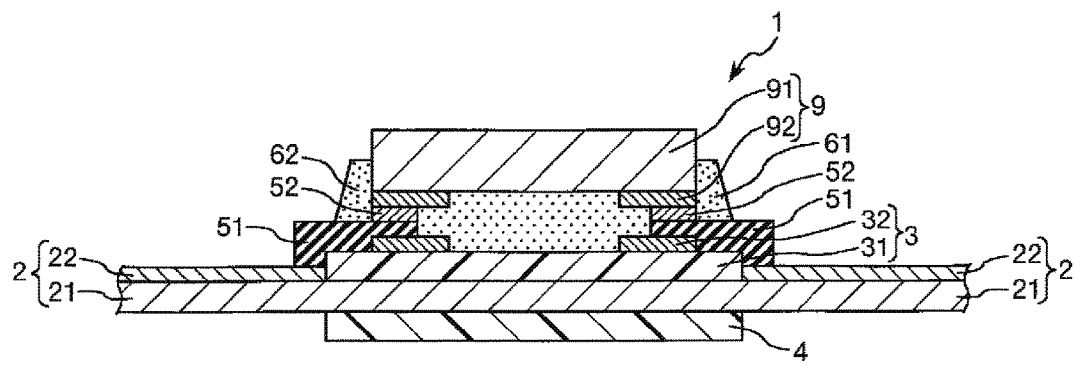
FIG. 6 is a sectional view of a detection device according to a second embodiment of the invention.

FIG. 6 is a sectional view of the detection device according to the second embodiment of the invention.

Hereinafter, the second embodiment will be described, but in the following description, differences from the above-described embodiment will be mainly described, and descriptions of similar contents will be omitted. In addition, in FIG. 6, the same reference numerals will be given to the same configurations as those in the embodiment described above.

In the above-described first embodiment, while the connection member 51 and the sensing section 9 are electrically connected to each other via the conductive portion 32 which penetrates the first base 3, in the embodiment, the connection member 51 is provided from the side to the upper surface of the first base 3. Therefore, the connection member 51 electrically connects the expanding and contracting base 2 and the first base 3 to each other, and the expanding and contracting base 2 and the sensing section 9 are electrically connected to each other via the connection member 52.

In addition, in the embodiment, the insulating section 31 of the first base 3 comes into contact with the expanding and contracting base 2 without passing through the mold portion. Therefore, it is possible to more reliably reinforce the expanding and contracting base 2 by the first base 3.

In addition, in the embodiment, a conductive material having elasticity is particularly preferably used as a configuration material of the connection member 51. The conductive material having elasticity is appropriately selected from, for example, the materials employed as the configuration material of the wiring 22 in the first embodiment. In addition, the conductive material maybe a conductive paste, a conductive film, or the like. By using the material, it is possible to mitigate the expansion and contraction of the expanding and contracting base 2 by the expansion and contraction of the connection member 51. Therefore, it is possible to more reliably prevent the connection member 51 from coming off from the expanding and contracting base 2.

Even in the second embodiment, the same effect as that in the above-described first embodiment can be obtained.

Third Embodiment

Next, a detection device according to a third embodiment of the invention will be described.

Figure 7:
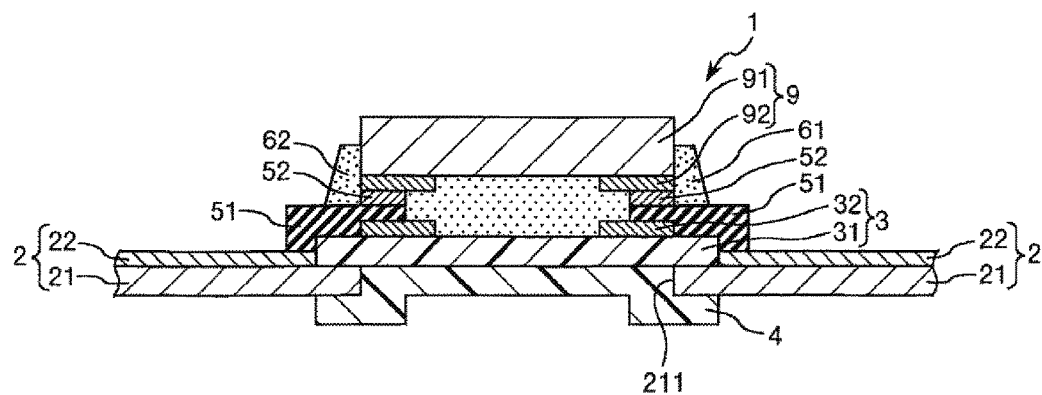
FIG. 7 is a sectional view of a detection device according to a third embodiment of the invention.

FIG. 7 is a sectional view of the detection device according to the third embodiment of the invention.

Hereinafter, the third embodiment will be described, but in the following description, differences from the above-described embodiment will be mainly described, and descriptions of similar contents will be omitted. In addition, in FIG. 7, the same reference numerals will be given to the same configurations as those in the embodiment described above.

The third embodiment is similar to the second embodiment except that the second base 4 is used as a coating film.

In other words, the second base 4 illustrated in FIG. 7 is a member (coating film) obtained by applying a liquid or paste-like raw material and curing or solidifying the material. By using the coating film, it is possible to further enhance the adhesion between the second base 4 and the expanding and contracting base 2. In other words, since a gap therebetween is unlikely to be generated, the reinforcing effect of the expanding and contracting base 2 by the second base 4 is further strengthened.

In addition, the expanding and contracting base 2 illustrated in FIG. 7 is provided with a through-hole 211 which penetrates the expanding and contracting insulating substrate 21 in the thickness direction. In addition, a part of the second base 4 is inserted into the through-hole 211. Accordingly, the second base 4 comes into contact with the first base 3 and puts the expanding and contracting base 2 between the first base 3 and the second base 4. As a result, the first base 3 and the second base 4 are integrated with each other to more firmly reinforce the expanding and contracting base 2.

Furthermore, at the position where the through-hole 211 is provided, the expansion and contraction of the expanding and contracting base 2 does not affect the first base 3 or the second base 4. Therefore, even when the expanding and contracting base 2 expands or contracts, the electric connection of the connection member 51, for example, becomes unlikely to receive an influence.

In addition, examples of the coating film include a raw material before curing of various thermosetting resins, such as a polyimide resin, an epoxy resin, and a phenol resin; and a raw material before solidifying of various thermoplastic resins, such as a polyamide resin, a polycarbonate resin, and polyethylene terephthalate.

Even in the third embodiment, the same effect as that in the above-described first and second embodiments can be obtained.

Fourth Embodiment

Next, a detection device according to a fourth embodiment of the invention will be described.

Figure 8:
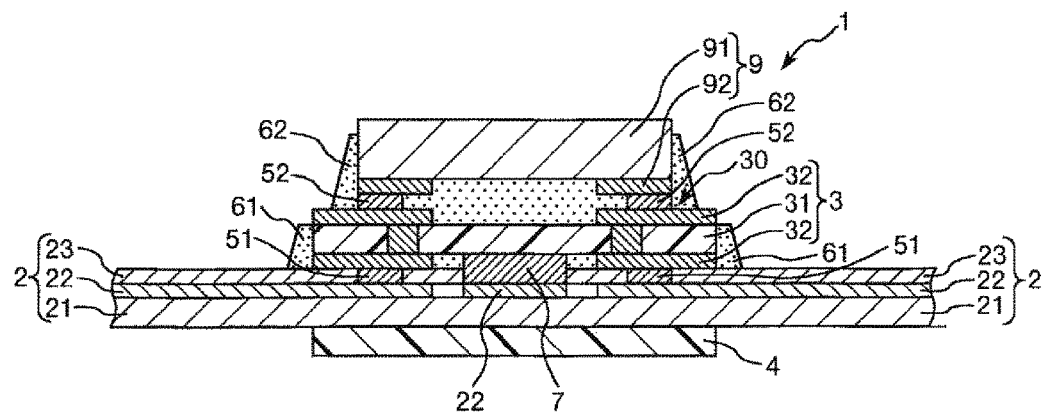
FIG. 8 is a sectional view of a detection device according to a fourth embodiment of the invention.

FIG. 8 is a sectional view of the detection device according to the fourth embodiment of the invention.

Hereinafter, the fourth embodiment will be described, but in the following description, differences from the above-described embodiment will be mainly described, and descriptions of similar contents will be omitted. In addition, in FIG. 8, the same reference numerals will be given to the same configurations as those in the embodiment described above.

The fourth embodiment is the same as the first embodiment except that a resin body 7 is provided between the expanding and contracting base 2 and the first base 3 and the configuration of the expanding and contracting base 2 is changed.

In other words, the detection device 1 illustrated in FIG. 8 is provided with the resin body 7 provided between the expanding and contracting base 2 and the first base 3. The resin body 7 is a member configured of a resin material, and is preferably provided so as to be directly in contact with both of the expanding and contracting base 2 and the first base 3. Accordingly, the resin body 7 functions as a spacer which maintains a constant distance between the expanding and contracting base 2 and the first base 3. Therefore, it is possible to suppress the expanding and contracting base 2 from deforming to the first base 3 side more than necessary, and to suppress occurrence of troubles due to deformation, for example, a loss of electric connection.

In addition, the configuration material of the resin body 7 is not particularly limited as long as the configuration material is a resin material, but the configuration material is appropriately selected from the materials described as the configuration materials of the expanding and contracting insulating substrate 21.

In addition, the expanding and contracting base 2 illustrated in FIG. 8 is provided with a cover layer 23 provided on the side opposite to the expanding and contracting insulating substrate 21 via the wiring 22. In other words, the wiring 22 is interposed between the expanding and contracting insulating substrate 21 and the cover layer 23.

By employing the structure, since it is possible to mechanically reinforce the wiring 22, it is possible to protect the wiring 22 from disconnection or resistance increase, and to enhance the reliability.

In addition, in particular, when the expanding and contracting base 2 is twisted, the probability of disconnection and the like can be lowered by sandwiching the wiring 22 between the expanding and contracting insulating substrate 21 and the cover layer 23.

Furthermore, since the wiring 22 is protected from external forces and the external environment, it is possible to suppress oxidation and the like of the wiring 22.

In addition, the cover layer 23 is not only a member to which a frame or the like is pasted but also a member formed by applying a liquid material and curing or solidifying the material.

The configuration material of the cover layer 23 is not particularly limited, but the configuration material of the cover layer 23 is appropriately selected from the materials described as the configuration materials of the expanding and contracting insulating substrate 21. In addition, the configuration material of the cover layer 23 may be different from the configuration material of the expanding and contracting insulating substrate 21, but may be the same. In a case where the configuration material of the cover layer 23 is the same as that of the expanding and contracting insulating substrate 21, when the expanding and contracting base 2 expands and contracts, the expanding and contracting insulating substrate 21 and the cover layer 23 can expand and contract in the same manner, and accordingly, the reliability of the detection device 1 is enhanced and the detection accuracy is improved.

Even in the fourth embodiment, the same effect as that in the above-described first embodiment can be obtained.

Fifth Embodiment

Next, a detection device according to a fifth embodiment of the invention will be described.

Figure 9:
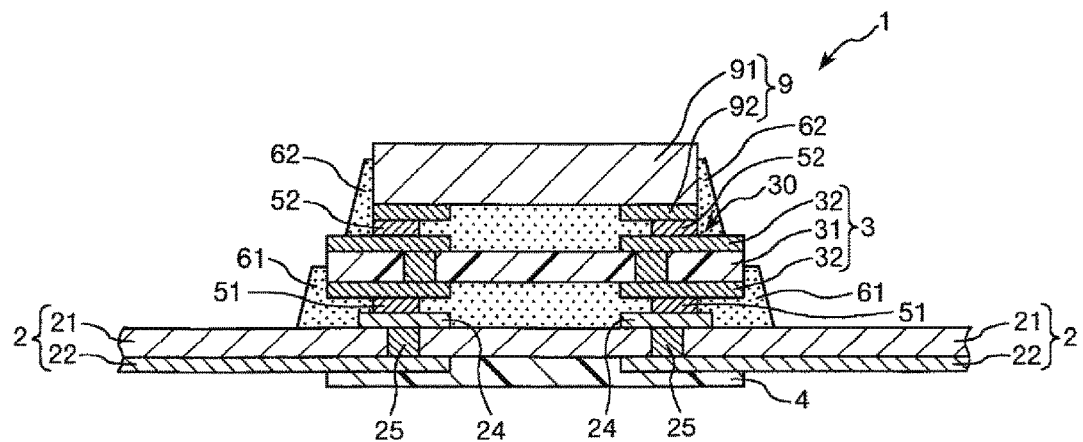
FIG. 9 is a sectional view of a detection device according to a fifth embodiment of the invention.

FIG. 9 is a sectional view of the detection device according to the fifth embodiment of the invention.

Hereinafter, the fifth embodiment will be described, but in the following description, differences from the above-described embodiment will be mainly described, and descriptions of similar contents will be omitted. In addition, in FIG. 9, the same reference numerals will be given to the same configurations as those in the embodiment described above.

The fifth embodiment is the same as the first embodiment except that the structure of the expanding and contracting base 2 is different.

In the above-described first embodiment, as illustrated in FIG. 3, while the wiring 22 is provided on the upper surface of the expanding and contracting insulating substrate 21, in the embodiment, as illustrated in FIG. 9, the wiring 22 is provided on the lower surface of the expanding and contracting insulating substrate 21.

In addition, the expanding and contracting base 2 illustrated in FIG. 9 includes an upper electrode 24 provided on the upper surface of the expanding and contracting insulating substrate 21 and a through wiring 25 which penetrates the expanding and contracting insulating substrate 21.

Therefore, the wiring 22 and the sensing section 9 are electrically connected to each other via the through wiring 25, the upper electrode 24, the connection member 51, the first base 3, and the connection member 52.

Even in the fifth embodiment, the same effect as that in the above-described first embodiment can be obtained.

In addition, in the embodiment, the disposition surface of the wiring 22 with respect to the expanding and contracting insulating substrate 21 is made different from that of the first embodiment, and accordingly, it is possible to make the stress generated in the wiring 22 when the expanding and contracting base 2 is curved in the thickness direction different.

In other words, in a case of FIG. 9, the wiring 22 extends more than the expanding and contracting insulating substrate 21, for example, when the both sides of the expanding and contracting base 2 are bent to be lifted up. Therefore, for example, in a case where the movement of the movable body to which the detection device 1 is mounted is large in such a manner as to bend both sides of the expanding and contracting base 2 illustrated in FIG. 9 to be lifted up, when the disposition illustrated in FIG. 9 is selected as the disposition of the wiring 22 with respect to the expanding and contracting insulating substrate 21, it is possible to further enhance the reliability of the detection device 1.

Meanwhile, for example, in a case where the movement of the movable body to which the detection device 1 is mounted is large in such a manner as to bend both sides of the expanding and contracting base 2 illustrated in FIG. 9 to be pressed down, when the disposition illustrated in FIG. 3 is selected as the disposition of the wiring 22 with respect to the expanding and contracting insulating substrate 21, it is possible to further enhance the reliability of detection device 1.

Sixth Embodiment

Next, a detection device according to a sixth embodiment of the invention will be described.

Figure 10:
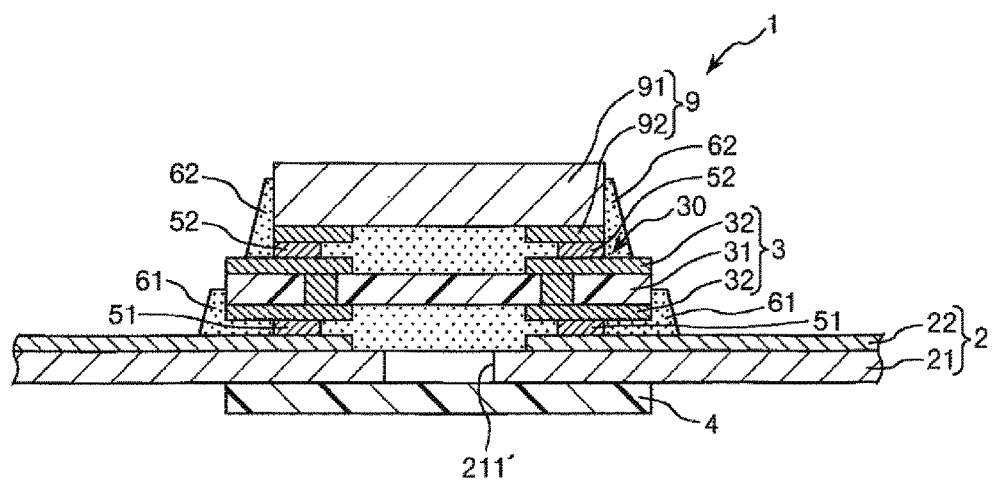
FIG. 10 is a sectional view of a detection device according to a sixth embodiment of the invention.

FIG. 10 is a sectional view of the detection device according to the sixth embodiment of the invention.

Hereinafter, the sixth embodiment will be described, but in the following description, differences from the above-described embodiment will be mainly described, and descriptions of similar contents will be omitted. In addition, in FIG. 10, the same reference numerals will be given to the same configurations as those in the embodiment described above.

The sixth embodiment is the same as the first embodiment except that the structure of the expanding and contracting base 2 is different.

In other words, the expanding and contracting base 2 illustrated in FIG. 10 is provided with a through-hole 211' which penetrates the expanding and contracting insulating substrate 21 in the thickness direction. Accordingly, at the position where the through-hole 211' in the expanding and contracting base 2 is provided, the expansion and contraction of the expanding and contracting base 2 becomes unlikely to affect the first base 3 or the second base 4. Therefore, even when the expanding and contracting base 2 expands or contracts, the electric connection of the connection member 51, for example, becomes unlikely to receive an influence.

Even in the sixth embodiment, the same effect as that in the above-described first embodiment can be obtained.

Seventh Embodiment

Next, a detection device according to a seventh embodiment of the invention will be described.

Figure 11:
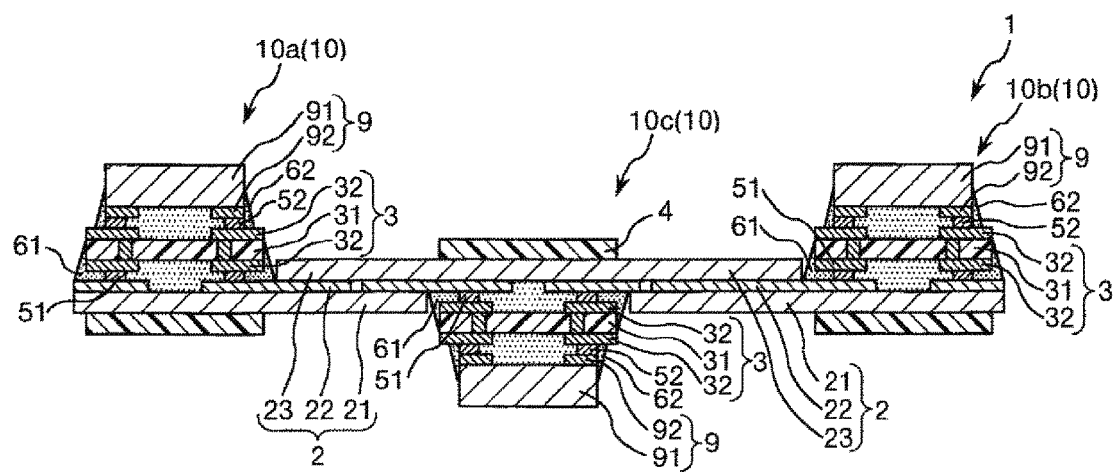
FIG. 11 is a sectional view of a detection device according to a seventh embodiment of the invention.

FIG. 11 is a sectional view of the detection device according to the seventh embodiment of the invention.

Hereinafter, the seventh embodiment will be described, but in the following description, differences from the above-described embodiment will be mainly described, and descriptions of similar contents will be omitted. In addition, in FIG. 11, the same reference numerals will be given to the same configurations as those in the embodiment described above.

The seventh embodiment is the same as the first embodiment except that the detection device 1 has a plurality of the first bases 3, the second bases 4, the sensing sections 9, and the like.

In other words, the detection device 1 illustrated in FIG. 11 includes the first base 3, the second base 4, the connection member 51, the connection member 52, the mold portion 61, the mold portion 62, and the sensing section 9 similar to the first embodiment. Here, these parts are collectively referred to as "unit 10".

The detection device 1 illustrated in FIG. 11 is a device provided with a plurality of units 10 (three units 10 in FIG. 11) for one expanding and contracting base 2.

Specifically, in the longitudinal direction of the expanding and contracting base 2, at the left end of FIG. 11, a first unit 10a which is the first unit 10 is provided.

Meanwhile, in the longitudinal direction of the expanding and contracting base 2, at the right end of FIG. 11, a second unit 10b which is the second unit 10 is provided.

In addition, in the longitudinal direction of the expanding and contracting base 2, in the vicinity of the center of FIG. 11, a third unit 10c which is the third unit 10 is provided.

In addition, the first unit 10a and the second unit 10b are disposed so that the sensing section 9 is positioned on the upper surface side of the expanding and contracting base 2. Meanwhile, the third unit 10c is disposed so that the sensing section 9 is positioned on the lower surface side of the expanding and contracting base 2.

In addition, the first unit 10a and the second unit 10b function as a motion sensor which detects the movement of a human from a change in resistance value of the wiring 22, similar to each of the above-described embodiments.

Meanwhile, when the detection device 1 is mounted on the human H, the third unit 10c can bring the sensing section 9 of the third unit 10c into contact with the surface of the human H. Therefore, in the sensing section 9 of the third unit 10c, an obtaining method of biological information (vital information), such as electrocardiogram, myoelectric potential, body temperature, blood pressure, heartbeat, and the like may be employed. Accordingly, the detection device 1 illustrated in FIG. 11 has both a function as a motion sensor and a function as a vital sensor.

By providing the plurality of units 10 having different functions in this manner, it is possible to realize the detection device 1 having a higher added value with more functions.

In addition, in the seventh embodiment, the same effect as that in the above-described first embodiment can be obtained.

In addition, the number of the units 10 installed on one expanding and contracting base 2 together is not particularly limited, and may be two, or may be four or more.

Eighth Embodiment

Next, a detection device according to an eighth embodiment of the invention will be described.

Figure 12:
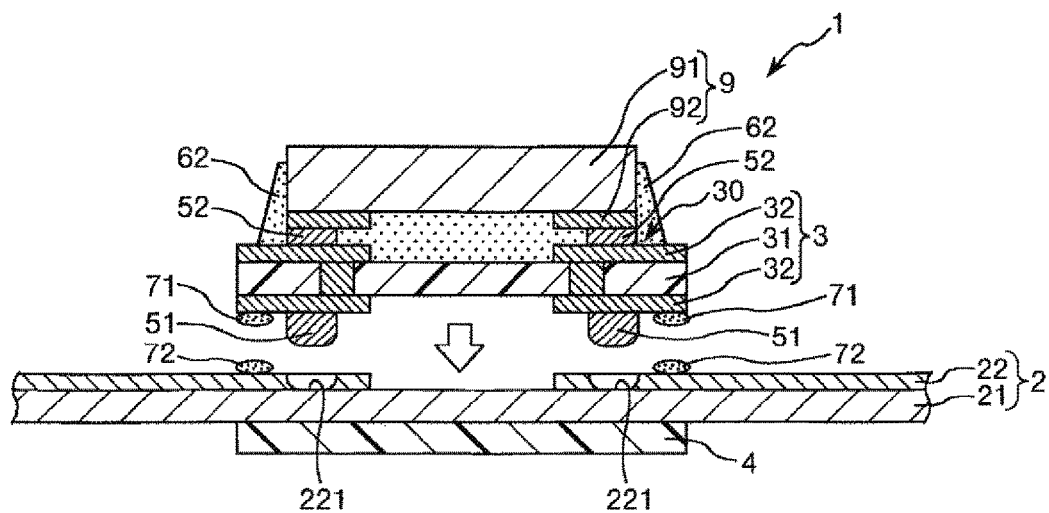
FIG. 12 is a sectional view of a detection device according to an eighth embodiment of the invention.

FIG. 12 is a sectional view of the detection device according to the eighth embodiment of the invention.

Hereinafter, the eighth embodiment will be described, but in the following description, differences from the above-described embodiment will be mainly described, and descriptions of similar contents will be omitted. In addition, in FIG. 12, the same reference numerals will be given to the same configurations as those in the embodiment described above.

The eighth embodiment is the same as the first embodiment except that the expanding and contracting base 2 and the first base 3 are attachable and detachable to and from each other.

In other words, in the eighth embodiment, as illustrated in FIG. 12, the expanding and contracting base 2 and the first base 3 can be separated from each other. When being separated as illustrated in FIG. 12, the connection member 51 is separated from the wiring 22 by releasing the fitted state with the recessed portion 221 formed in the wiring 22.

Meanwhile, between the expanding and contracting base 2 and the first base 3 illustrated in FIG. 12, two pairs of fixing units configured with a first magnet 71 and a second magnet 72 are provided. In other words, the first magnet 71 is provided on the lower surface of the first base 3 in FIG. 12, and meanwhile, the second magnet 72 is provided on the upper surface of the expanding and contracting base 2 in FIG. 12. Since a magnetic suction force acts between the first magnet 71 and the second magnet 72, it is possible to fix the expanding and contracting base 2 and the first base 3 to each other accordingly.

In addition, by pulling the magnets each other with a force that exceeds the magnetic suction force, it is possible to easily separate the first base 3 from the expanding and contracting base 2. Therefore, for example, when exchanging the expanding and contracting base 2 or the first base 3 for a new base, it is possible to easily perform the exchange work by separating the expanding and contracting base 2 and the first base 3 from each other.

In addition, in FIG. 12, the mold portion 61 is omitted.

In addition, the fixing unit is not limited to the above-described configuration, and for example, a configuration using a clamp or the like may be employed, or a configuration that uses members that are engaged with each other may be employed.

Meanwhile, the first base 3 and the sensing section 9 maybe attachable and detachable to and from each other. In other words, by providing the above-described fixing unit between the first base 3 and the sensing section 9, the sensing section 9 may be easily separated from the first base 3. Accordingly, for example, when exchanging the sensing section 9 for a new base, it is possible to easily perform the exchange work by separating the first base 3 and the sensing section 9 from each other.

In addition, in the eighth embodiment, the same effect as that in the above-described first embodiment can be obtained.

Ninth Embodiment

Next, a detection device according to a ninth embodiment of the invention will be described.

Figure 13:
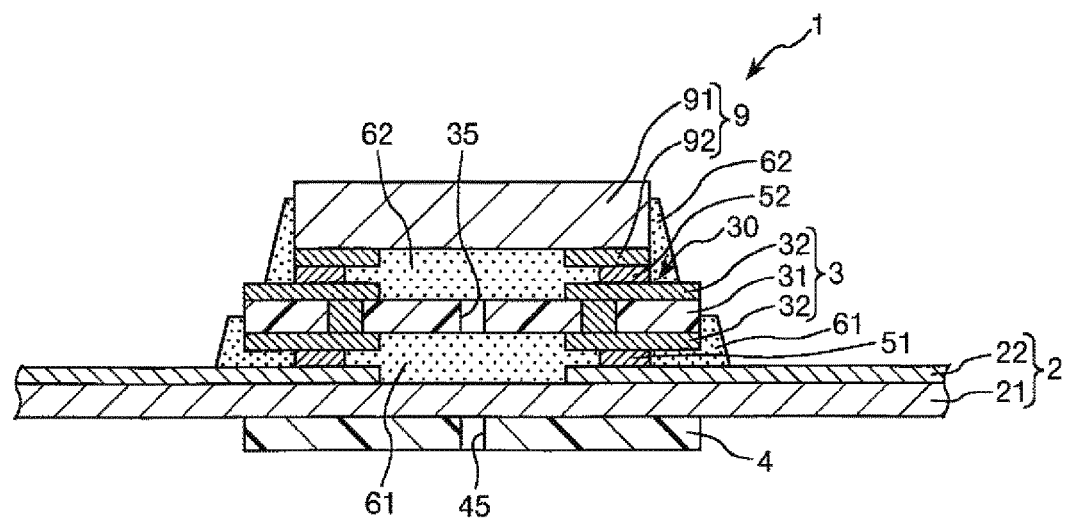
FIG. 13 is a sectional view of a detection device according to a ninth embodiment of the invention.

FIG. 13 is a sectional view of the detection device according to the ninth embodiment of the invention.

Hereinafter, the ninth embodiment will be described, but in the following description, differences from the above-described embodiment will be mainly described, and descriptions of similar contents will be omitted. In addition, in FIG. 13, the same reference numerals will be given to the same configurations as those in the embodiment described above.

The ninth embodiment is the same as the first embodiment except that through-holes are respectively provided in the first base 3 and the second base 4.

In other words, the first base 3 illustrated in FIG. 13 has a through-hole 35 which penetrates therethrough. By providing the through-hole 35, for example, when bonding the first base 3 to the expanding and contracting base 2 while positioning the first base 3, it is necessary to position the first base 3 while confirming the position of the expanding and contracting base 2 via the through-hole 35.

Specifically, for example, when an alignment mark is provided on the expanding and contracting base 2, the first base 3 is positioned so that the alignment mark can be seen from the through-hole 35. Accordingly, it is possible to accurately and easily perform the positioning, and to further improve the reliability of the detection device 1.

In addition, when the mold portion 61 fills the space between the expanding and contracting base 2 and the first base 3, the mold portion 61 can be injected via the through-hole 35. Accordingly, it is possible to efficiently perform the filling operation, and the mold portion 61 can be easily filled up to every corner.

Meanwhile, the second base 4 illustrated in FIG. 13 has a through-hole 45 which penetrates therethrough. By providing the through-hole 45, for example, when bonding the second base 4 to the expanding and contracting base 2 while positioning the second base 4, it is possible to position the second base 4 while confirming the position of the expanding and contracting base 2 via the through-hole 45.

Specifically, for example, when an alignment mark is provided on the expanding and contracting base 2, the second base 4 is positioned so that the alignment mark can be seen from the through-hole 45. Accordingly, it is possible to accurately and easily perform the positioning, and to further improve the reliability of the detection device 1.

In addition, when the adhesive (not illustrated) fills the space between the expanding and contracting base 2 and the second base 4, the adhesive can be injected via the through-hole 45. Accordingly, it is possible to efficiently perform the injection operation.

In addition, in the ninth embodiment, the same effect as that in the above-described first embodiment can be obtained.

In addition, it is not necessary to inject the adhesive to the entire space between the expanding and contracting base 2 and the second base 4, and may be injected only to a part thereof.

In addition, both of the through-hole 35 and the through-hole 45 may be provided, but only one of the holes may be provided.

Above, although the detection device according to the invention has been described based on the embodiments, the invention is not limited thereto, and the configuration of each portion can be replaced with an arbitrary configuration having similar functions. In addition, any other constituent may be added to the invention. Further, each embodiment may be appropriately combined with each other.

In addition, in the above-described embodiment, a configuration in which a sticking portion is provided on the expanding and contracting base and the detection device can be fixed to the living body by sticking the sticking portion to the living body, is described, but the method for fixing the detection device to the living body is not particularly limited. For example, by turning a band portion around the arm or the like of the living body, the detection device may be fixed to the living body, the detection device itself does not have the sticking portion, and the detection device can be fixed to the living body via a sticking member, such as a sticking tape.

In addition, in the above-described embodiment, although the configuration that uses the detection device for a human is described, the target which uses the detection device is not limited to a living body, but may be, for example, a dead body, various animals other than humans, or insects, or may be a plant. In addition, the target may be various artifacts other than life forms.

The entire disclosure of Japanese Patent Application No. 2017-057440, filed Mar. 23, 2017 is expressly incorporated by reference herein.

What is claimed is:

1. A detection device comprising:
   an expanding and contracting base having elasticity;
   a first base which is provided so as to overlap the expanding and contracting base, has a Young's modulus higher than that of the expanding and contracting base, and includes a connection portion to which a sensing section is connectable;
   a second base which is provided on a side of the expanding and contracting base opposite to the first base, and has a Young's modulus higher than that of the expanding and contracting base;
   a connection member which electrically connects the expanding and contracting base and the first base to each other;
   a mold portion which is provided to come into contact with the connection member, has a Young's modulus higher than that of the expanding and contracting base, and has a Young's modulus lower than that of the first base; and
   a wiring having elasticity which is provided on the expanding and contracting base,
   wherein the wiring has a recessed portion, and the connection member is fitted into the recessed portion.

2. The detection device according to claim 1, further comprising:
   a sensing section which is connected to the connection portion and detects a change in electric resistance of the wiring.

3. The detection device according to claim 1,
   wherein the second base is a coating film.

4. The detection device according to claim 1,
   wherein the mold portion is provided to come into contact with the connection member, the expanding and contracting base, and the first base.

5. The detection device according to claim 1, wherein the connection member is provided between the expanding and contracting base and the first base.

6. The detection device according to claim 1, wherein, the first base, the second base, the connection member, and the mold portion define a unit, and a plurality of the units are located on the expanding and contracting base.

7. The detection device according to claim 1, which is a vital sensor.

8. The detection device according to claim 1, which is a motion sensor.

* * * * *